US012478754B2

(12) United States Patent
Eifler

(10) Patent No.: US 12,478,754 B2
(45) Date of Patent: Nov. 25, 2025

(54) MASK BEAD

(71) Applicant: Loewenstein Medical Technology S.A., Luxembourg (LU)

(72) Inventor: Martin Eifler, Glueckstadt (DE)

(73) Assignee: Loewenstein Medical Technology S.A., Luxembourg (LU)

( * ) Notice: Subject to any disclaimer, the term of this patent is extended or adjusted under 35 U.S.C. 154(b) by 280 days.

(21) Appl. No.: 18/317,275

(22) Filed: May 15, 2023

(65) Prior Publication Data

US 2023/0277796 A1 Sep. 7, 2023

Related U.S. Application Data

(63) Continuation of application No. 16/380,313, filed on Apr. 10, 2019, now Pat. No. 11,679,220.

(30) Foreign Application Priority Data

Apr. 12, 2018 (DE) ........................ 102018002998.1

(51) Int. Cl.
*A61M 15/06* (2006.01)
*A61M 16/06* (2006.01)

(52) U.S. Cl.
CPC .... *A61M 16/0683* (2013.01); *A61M 16/0616* (2014.02); *A61M 2210/0618* (2013.01)

(58) Field of Classification Search
CPC .......... A61M 16/0622; A61M 16/0611; A61M 16/0604; A61M 16/0605; A61M 16/06
See application file for complete search history.

(56) References Cited

U.S. PATENT DOCUMENTS

| | | | |
|---|---|---|---|
| 2002/0148472 | A1 | 10/2002 | Barnett |
| 2008/0257354 | A1 | 10/2008 | Davidson |
| 2009/0139526 | A1 | 6/2009 | Melidis |
| 2012/0138062 | A1 | 6/2012 | Ho |
| 2014/0144448 | A1 | 5/2014 | Eifler |
| 2014/0283842 | A1 | 9/2014 | Bearne |
| 2016/0082214 | A1 | 3/2016 | Barlow |
| 2016/0184544 | A1 | 6/2016 | Patel |
| 2018/0185598 | A1 | 7/2018 | Olsen |
| 2018/0272095 | A1 | 9/2018 | Eves |

FOREIGN PATENT DOCUMENTS

| | | | |
|---|---|---|---|
| DE | 102007057091 | A1 | 6/2008 |
| DE | 102013019149 | A1 | 6/2014 |
| EP | 1982740 | A2 | 10/2008 |
| WO | 0162326 | A1 | 8/2001 |
| WO | 2014183167 | A1 | 11/2014 |
| WO | 2015020535 | A1 | 2/2015 |
| WO | 2016032343 | A1 | 3/2016 |
| WO | 2017049360 | A1 | 3/2017 |

*Primary Examiner* — Margaret M Luarca
(74) *Attorney, Agent, or Firm* — Abel Schillinger, LLP

(57) ABSTRACT

The present invention relates to a mask bead for a patient interface, comprising a nose bridge region, at least one side region, a base region, a mask bead attachment, and a bearing region on the patient. The bearing region extends from the side regions and the base region and also the nose bridge region to an opening and is designed as a sealing lip which frames the central opening which serves at least for the introduction of the nose of the patient. The mask bead is formed from at least one elastic material and comprises at least one support structure in the mask bead, which support structure is designed to in part face the bearing region and to in part face the mask bead attachment.

20 Claims, 6 Drawing Sheets

MASK BEAD

CROSS-REFERENCE TO RELATED APPLICATIONS

The present application is a continuation of U.S. patent application Ser. No. 16/380,313, filed on Apr. 10, 2019, which claims priority under 35 U.S.C. § 119 of German Patent Application No. 102018002998.1 filed on Apr. 12, 2018. The entire disclosures of these two applications are expressly incorporated by reference herein.

BACKGROUND OF THE INVENTION

1. Field of the Invention

The present invention relates to a bead for a mask such as, e.g., a mask used for ventilation and sleep therapy.

2. Discussion of Background Information

Masks are used in ventilation and sleep therapy, where a patient is supplied with respiratory gas by means of a flow source or pressure source. A mask represents the interface between patient and appliance. It is composed in most cases of a mask body with a mask bead and is fastened on the patient's head by means of a harness and possibly with an additional forehead support. The mask body is generally made of a relatively stiff plastic, and the mask bead, which bears on the face or on parts of the face of the patient, is made of a relatively thin, soft material, preferably a skin-compatible silicone, a thermoplastic elastomer (TPE) or polyurethane, and it generally has a sealing lip in order to ensure a sufficient seal and to prevent leakage.

The function of a mask bead is, among other things, to support the weight of the mask body gently against the face. For this purpose, the mask bead has a strength which allows it to support the mask body but which, by virtue of the relatively soft material of the mask bead, is able to protect the sensitive parts of the patient's face.

As described at the outset, conventional mask beads are made of a relatively thin, soft material of fairly low strength, so as to afford the greatest possible level of comfort to a patient wearing a corresponding mask, and so as to achieve a high degree of adaptability of the mask bead to the facial contours of the patient.

However, the solutions known from the prior art have the disadvantage that the reduced strength of the material of the mask bead also leads to a reduced supporting function of the mask bead. Thus, although the reduced strength of the material improves the comfort of the mask bead and its adaptability to the facial contours of the patient, a reduction in strength at the same time also leads to deterioration of the supporting function of the mask bead.

In view of the foregoing it would be advantageous to have available a mask bead which improves both the wearing comfort experienced by a patient and the adaptability of the mask bead to the facial contours of the patient, and which at the same time also improves the supporting function of the mask bead.

SUMMARY OF THE INVENTION

The present invention provides a mask bead for a patient interface, comprising a nose bridge region, at least one side region, a base region, a mask bead attachment, and a bearing region on the patient. The bearing region extends from the side regions and the base region and also the nose bridge region to the opening and is designed as a sealing lip which frames the central opening which serves at least for the introduction of the nose of the patient. The mask bead according to the invention can be used both for nasal masks and for full-face masks.

The mask bead can be divided into nose bridge region, side regions and a base region.

Nose bridge region designates the region of the mask bead having a convexity with an angle>180°. The nose bridge region typically has a wall thickness of from about 0.2 mm to about 0.7 mm. The nose bridge region generally extends from the bearing region in the direction of the mask bead attachment.

Base region designates a region of the mask bead which is formed at a side of the mask bead opposite the nose bridge region and has a substantially linear extent. For example, the base region has a wall thickness of from about 0.5 mm to about 1.2 mm. The base region generally extends from the bearing region in the direction of the mask bead attachment.

Side region designates a region of the mask bead which extends, on a respective side of the opening of the mask bead, between the nose bridge region and the base region, wherein the two side regions have a tapering or conical shape with respect to each other. For example, the side region has a wall thickness of from about 1.2 mm to about 2.5 mm. The side regions each extend from the bearing region in the direction of the mask bead attachment. Optionally, the mask bead can have a double lip structure.

The nose bridge region and the base region each adjoin the side regions, wherein respective transition regions are formed between nose bridge region and side regions and between base region and side regions. A transition region is a region in which the profile of the shape of the mask bead changes. The transition region between the nose bridge region and the respectively adjacent side region is the region in which the angle of the mask bead transitions from a curved shape, having an angle of more than 180°, to a linear shape. The transition region between base region and side region is in each case the region in which the mask bead transitions at an angle of more than 90° from a conically tapering shape to a linear profile.

According to the invention, the mask bead is formed from at least one elastic material and comprises at least one support structure, wherein the support structure in the mask bead is designed facing the bearing region in part and facing the mask bead attachment in part. Over its course, the support structure can have different distances from the bearing region. For example, the support structure, at a vertex of the nose bridge region, can have a greater distance from the bearing region than it has at a lateral region of the nose bridge region. Moreover, the support structure, in at least one side region of the mask bead, can have at least two different distances from the bearing region. For example, the support structure, in a central region of a side region, can have a greater distance from the bearing region than it does at the transition points to the nose bridge region or to the base region. The bearing region can differ from the nose bridge region, the side regions or the base region by having a wall thickness in the range of from about 0.2 mm to about 0.75 mm, for example. Alternatively, the bearing region has about the same wall thickness as the nose bridge region, the side regions or the base region.

The mask bead is made of a skin-compatible material, preferably of silicone in a Shore hardness range of from about 35 to about 65 Shore A, preferably of about 40-60 Shore A.

The mask bead can be produced in one piece or in a multi-component injection molding process, for example a two-component process. In the case of production in a two-component process, the mask bead is produced from materials with different degrees of hardness, for example with a softer material being injected onto a harder material. By production in a multi-component process, a mask bead with different material properties can be produced, as a result of which a mask bead can be produced that is sufficiently stiff and yet resilient. The mask bead can be formed of at least two material thicknesses, for example three, four or five different material thicknesses. The contacting of the different components is preferably achieved by adhesion of the materials. Alternatively or additionally, mechanical contact points can strengthen the adhesion (positive locking).

The support structure is generally formed integrally in the mask bead. Alternatively, the support structure can be configured as an element mounted on an inner or outer wall of the mask bead. The support structure is generally designed to have a wall thickness which differs from the wall thickness of the surrounding mask bead or of the individual regions (nose bridge region, side regions, base region). In particular, the support structure has a wall thickness that is in a range of from about 1/12 to about 1/8 thicker, in particular about 1/10 thicker, than the wall thickness of the surrounding mask bead or of the respective regions. For example, if it is about 1/10 thicker compared to the surrounding material in the region of the nose bridge region of the mask bead, the support structure can have a wall thickness in the range of from about 0.33 mm to about 0.77 mm.

Typically, the support structure is completely filled. In an alternative embodiment, the support structure can be at least partially filled. The support structure can have a homogeneously filled structure. Alternatively, the support structure can have an internal shape that supports the support function of the support structure. Optionally, the support structure can be configured as a sealing structure which is designed to seal the mask bead at the bearing region with respect to a patient's face.

In a development of the invention, the support structure surrounds the opening at least by two thirds or completely. In an embodiment in which the support structure surrounds the opening of the mask bead by at least two thirds, the nose bridge region and the side regions of the mask bead generally have the support structure, while the base region of the mask bead is designed free of the support structure. By virtue of the opening of the mask bead being enclosed by the support structure by at least two thirds, the mask bead can be optimally supported. In the case where the opening of the mask bead is surrounded completely by the support structure, the support structure is additionally formed in the base region. The complete enclosure affords the possibility of a particularly uniform distribution of weight across the facial regions of the patient.

In one embodiment, the support structure has at least two reinforcement points and at least one connecting structure between two reinforcement points. Generally, the support structure is of a continuous configuration, wherein the support structure comprises at least two reinforcement points and at least one connecting structure that connects the two reinforcement points. The strength of the mask bead is increased by the design of the support structure. The connecting structure can be linear or curved. Alternatively, the connecting structure can have an undulating, indented or curved structure.

The support structure can have a wall thickness that is continuously the same. Generally, the support structure has different wall thicknesses in the individual regions. Generally, the support structure has a wall thickness that is about 1/12 to about 1/8 thicker, in particular about 1/10 thicker, than the respective region in which it is formed.

Generally, the support structure additionally has a width that is continuously the same. The width of the support structure is the cross section of the support structure of the mask bead when the latter is fitted in place in a horizontal direction. Optionally, the width of the support structure can be of a different design. For example, the width of the support structure can be reduced in the region of at least one reinforcement point.

In a further embodiment, the at least one connecting structure is designed as an arch, wherein the arch is designed facing away from the bearing region. The arch extends, for example, from one reinforcement point to a second reinforcement point across the nose bridge region. Preferably, the reinforcement points are each arranged at a transition between nose bridge region and side region. Optionally or additionally, the arch extends across the side region of the mask bead from one reinforcement point to a further reinforcement point, which is formed at the transition from the side region to the base region of the mask bead. Alternatively or additionally, the arch extends across the base region of the mask bead from the reinforcement point at the transition of the side region to a further reinforcement point, which is formed at the transition of the base region to the side region of the mask bead. The arch-shaped configuration of the connecting structure permits a particularly stable and uniform distribution of the weight of the mask body. The arch gives strength to a region of the mask bead across which it is formed and it can therefore also be designated as a strengthening structure.

In a development of the mask bead according to the invention, the reinforcement points in the mask bead are arranged in the region of the bearing region or are arranged lying on the bearing region. The reinforcement points are generally free of contact with the bearing region of the mask bead. By virtue of the contact-free design, the support structure does not bear directly on the patient's face, as a result of which the regions coming directly into contact with the patient can be provided with a softer or thinner material. Alternatively, the reinforcement point of the support structure can be formed on the bearing region or lying on the bearing region.

In a further development, starting from at least one connecting structure of the support structure, a supporting element is formed which widens in the direction of the mask bead attachment. The supporting element is designed to support the pressure acting on the support structure through the weight of the mask bead in the fitted state of the mask bead. The supporting element generally starts from the connecting structure, which is configured as an arch, for example. The supporting element can have an hourglass shape. The supporting element can be configured as a spacer element, which is designed to provide a space between the support structure and the mask bead attachment.

In one embodiment, the supporting element is formed centrally or running laterally from the connecting structure. In a central arrangement of the supporting element, a pressure of the support structure is carried off in a uniform manner. A central arrangement of the supporting element additionally permits the formation of adjustment regions of identical size. The adjustment regions can be U-shaped or V-shaped kink regions. The central arrangement of the supporting element is particularly stable, wherein the adjustment region is uniformly adjustable both in the direction of the nose bridge region and also in the direction of the base region and/or is tiltable with respect to a perpendicular of the mask bead in the fitted state. This has the advantage that the mask bead is adaptable to a facial contour of the patient, in particular to a shape of the nose bridge of the patient.

A lateral arrangement of the supporting element permits the formation of two adjustment regions of different sizes. The adjustment regions can have U-shaped or V-shaped kink regions. The lateral arrangement of the supporting element thus permits the formation of a first, larger adjustment region and a second, smaller adjustment region, wherein the first adjustment region is preferably formed in the region of the nose bridge region and the second adjustment region is preferably formed in the region of the base region. By virtue of the formation of two adjustment regions of two different sizes, the mask bead can be strongly tilted to differing extents along the perpendicular of the mask bead in the fitted state. This has the advantage that, on account of the larger adjustment region in the region of the nose bridge region, the mask bead is more strongly tiltable in this region and is thus adaptable to a larger number of different facial contours or nose bridge contours.

In a development according to the invention, at least one kink region is formed at at least one transition of the support structure to the supporting element. The kink region can be U-shaped or V-shaped. The kink region is preferably formed at an adjustment region, such that the adjustment of the adjustment region is effected through the movement of the kink region. A kinking or pressing together of the kink region is brought about mostly as the mask bead is placed onto, fastened and adjusted on the patient's face. During the kinking of the kink region, the adjustment region is pressed together in such a way that it forms a convexity in the direction of the outside of the mask bead. The larger the adjustment region, the greater the pressure, hence the greater the convexity. The kink region can be formed by a reduction of the wall thickness of the support structure or of the supporting element. Alternatively, the kink region can be formed by a spring structure. Alternatively, the kink region can be formed by means of a softer material compared to the material of the support structure or of the supporting element.

In a further development, at least one of the kink regions is formed by a reduction of the thickness of the support structure. By means of the reduction of the wall thickness of the support structure, a V-shaped kink region is formed. Of particular advantage is the embodiment with a lateral kink region, through a laterally arranged supporting element. Alternatively, at least one of the kink regions can be formed by a reduction of the width of the support structure.

In one embodiment, the support structure and at least one kink region form at least one adjustment region. The adjustment region generally has a wall thickness of from about 0.2 mm to about 0.7 mm, in particular of from about 0.3 mm to about 0.5 mm. The kink region is preferably formed by the support structure and the supporting element. The adjustable adjustment region is formed by the mobility of the kink region. The thicker the kink region, the more the adjustment region can be adjusted or tilted.

In a further embodiment, the reinforcement points are formed at the transition of the nose bridge region to the side region and/or at the transition of the base region to the side region. Alternatively, the reinforcement points are arranged in the nose bridge region, in the side region or in the base region. Generally, the mask bead comprises two to eight reinforcement points, preferably four reinforcement points.

In one embodiment, the reinforcement points of the support structure are arranged in at least one side region.

In a further embodiment, at least one connecting structure is formed over the nose bridge region of the mask bead, wherein the reinforcement points delimiting the connecting structure are arranged at side regions of the mask bead separated by the opening. The arrangement of the reinforcement points to the side of the opening has the advantage that a stable structure can be formed over the nose bridge region.

In a further embodiment of the invention, at least one connecting structure is formed over a side region of the mask bead, wherein the reinforcement points delimiting the connecting structure are arranged on a common side region of the mask bead. The arrangement of the reinforcement points on a common side or on a common side region has the advantage that a stable structure can be formed over a non-sensitive side region.

In one embodiment, the support structure has a wall thickness that is about 1/12 to about 1/8 thicker, in particular about 1/10 thicker, than the respective region in which it is formed. The support structure can in this case have different wall thicknesses. Optionally, the support structure has a smaller wall thickness in a part of the support structure adjacent to the nose bridge region than in a part of the support structure adjacent to the base region.

In one development, the support structure has a wall thickness of from about 2 mm to about 1.8 mm, and the surrounding mask bead wall has a wall thickness of about 1.6 mm. The support structure in this case has a wall thickness of about 1.8 mm in the part of the support structure adjacent to the nose bridge region and a wall thickness of about 2 mm in the part of the support structure adjacent to the base region.

In one embodiment, the support structure has at least two reinforcement points and at least one connecting structure between two reinforcement points, wherein the at least one connecting structure is designed as an arch, wherein the arch is designed facing away from the bearing region.

In one development, at least one kink region is formed at at least one transition of the support structure to the supporting element, wherein the support structure and the at least one kink region form at least one adjustment region, wherein the adjustment region has a wall thickness of from about 0.2 mm to about 0.7 mm, in particular of from about 0.3 mm to about 0.5 mm.

The present invention moreover relates to a mask bead for a patient interface, consisting of a nose bridge region, at least one side region, a base region, a mask bead attachment, and a bearing region on the patient, wherein the bearing region extends from the side regions and the base region and also the nose bridge region to the opening, wherein the bearing region is designed as a sealing lip which frames the central opening serving at least for the introduction of the nose of the patient.

According to the invention, the mask bead comprises at least one support structure and at least one kink region, wherein the support structure and the at least one kink region form at least one adjustment region, wherein the adjustment region has a wall thickness of from about 0.2 mm to about 0.7 mm, in particular of from about 0.3 mm to about 0.5 mm.

The present invention moreover relates to a mask bead for a patient interface, consisting of a nose bridge region, at least one side region, a base region, a mask bead attachment, and a bearing region on the patient, wherein the bearing region extends from the side regions and the base region and also the nose bridge region to the opening, wherein the bearing region is designed as a sealing lip which frames the central opening serving at least for the introduction of the nose of the patient.

According to the invention, the mask bead comprises at least one support structure, wherein the support structure has a wall thickness of from about 2 mm to about 1.8 mm, the nose bridge region has a wall thickness of about 0.2-0.7 mm, in particular about 0.35 mm, the base region has a wall thickness of about 0.5-1.2 mm, in particular about 0.6 mm, and the side region has a wall thickness of 1.2-2.5 mm, in particular 1.6 mm.

BRIEF DESCRIPTION OF THE DRAWINGS

Preferred illustrative embodiments of the invention are explained in more detail below with reference to highly simplified schematic drawings, in which.

In the drawings, the same structural elements in each case have the same reference numerals.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
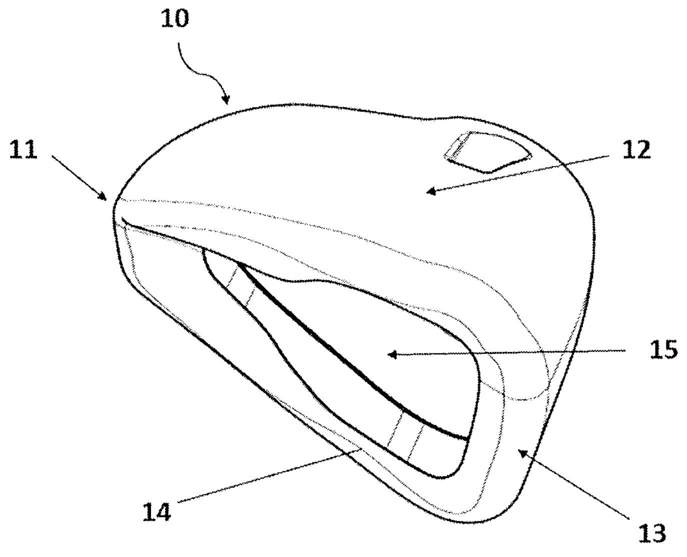
FIG. 1 shows a perspective side view of a mask bead according to the invention, with a support structure (not shown)

FIG. 1 shows a perspective side view of a mask bead 10 according to the invention with a support structure (not shown). The figure shows a bearing region 14 surrounding an opening 15, a nose bridge region 11, a side region 12 and a base region 13 of the mask bead 10. The bearing region 14 is designed as a sealing lip and encloses the whole opening 15. The mask bead has different wall thicknesses in the nose bridge region 11, in the side region 12 and in the base region 13.

Figure 2:
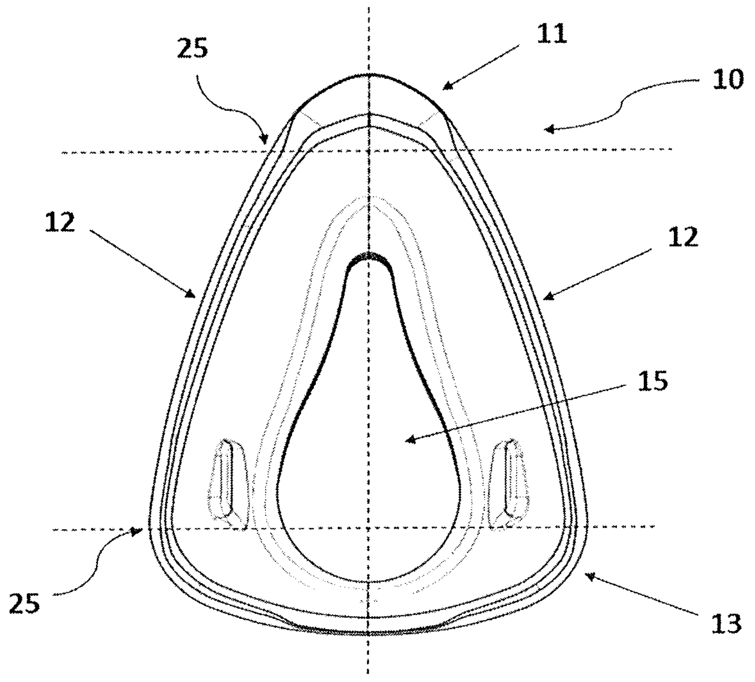
FIG. 2 shows a schematic plan view of the mask bead according to the invention, depicting the nose bridge region, two side regions and a base region.

FIG. 2 shows a schematic plan view of the mask bead 10 according to the invention, depicting the nose bridge region 11, two side regions 12 and a base region 13 of the mask bead 10. The nose bridge region 11 is a region located opposite the base region 13. The two side regions 12, separated by the opening 15, are arranged between the nose bridge region 11 and the base region 13. The opening 15 is configured to receive at least partially the nose of a patient.

The nose bridge region 11 is a region of the mask bead 10 in which the latter has a convexity with an angle of >180°. The base region 13 is a region of the mask bead 10 lying opposite the nose bridge region 11 and having a substantially linear extent. The side region 12 is a region of the mask bead 10 extending between the nose bridge region 11 and the base region 13. The mask bead 10 thus has two side regions 12, which are arranged lying opposite each other and separated by an opening 15. The two side regions 12 have a conical shape with respect to each other.

The various regions (nose bridge region 11, side regions 12 and base region 13) are connected to one another by transition regions 25. The transition region 25 between the nose bridge region 11 and a side region 12 is the region where the angle of the mask bead 10 transitions from an arc shape into a linear shape. The transition region 25 between base region and side region is the region in which the mask bead transitions from the conical shape at an angle of more than 90° into a linear profile.

Overall, in the present embodiment, the nose bridge region 11, the side region 12 and the base region 13 are configured in an approximate size ratio of 1:1:3. Optionally, the chosen size ratios can be different.

Figure 3:
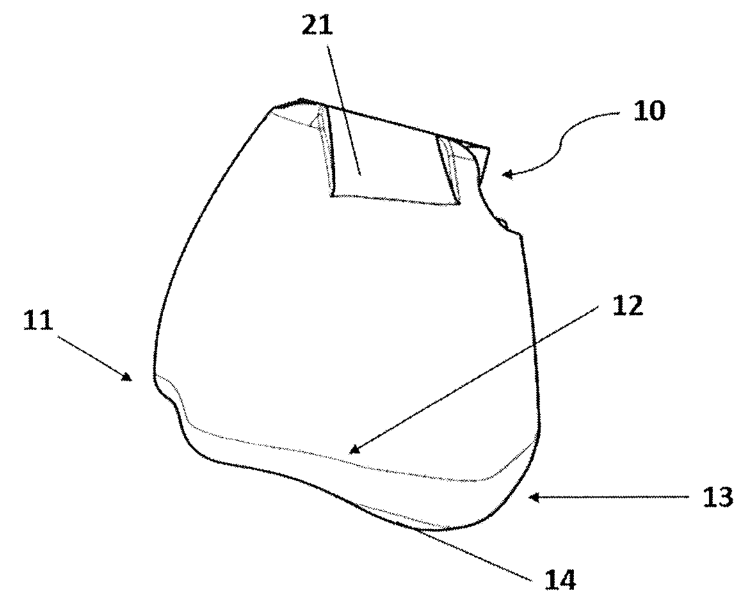
FIG. 3 shows a side view of the mask bead according to the invention.

FIG. 3 shows a side view of the mask bead 10 according to the invention. It shows the nose bridge region 11, the side region 12, the base region 13 and the bearing region 14. The bearing region 14 extends peripherally about an opening (not shown) of the mask bead 10. Opposite the bearing region 14, a mask bead attachment 21 is formed which is configured to attach the mask bead 10 to a hose system or for example to a forehead support.

Figure 4:
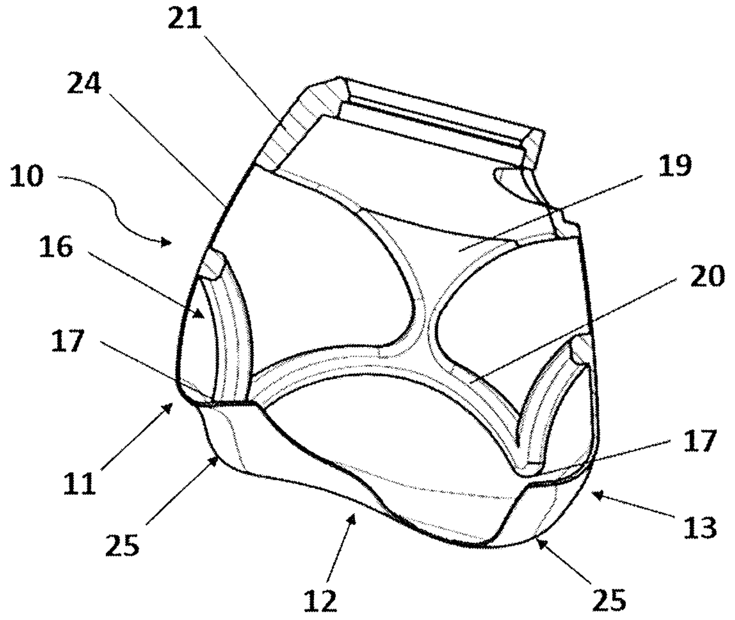
FIG. 4 shows a longitudinal section through the mask bead according to the invention, with a support structure and a supporting element.

FIG. 4 shows an axial longitudinal section through the mask bead 10 according to the invention shown in FIGS. 1 to 3, with a support structure 16 and a supporting element 19. The longitudinal section thus shows an inner view of the mask bead 10 when fitted in place in a vertical direction. The figure shows the mask bead 10 with the mask bead attachment 24, the nose bridge region 11, the side region 12, the base region 13 and the mask bead attachment 24.

In the present embodiment of the mask bead 10 according to the invention, the support structure 16 comprises at least two reinforcement points 17 which are arranged, respectively, in a transition region 25 from the nose bridge region 11 to the side region 11 or from the side region 12 to the base region 13, and also an arch-shaped connecting structure 20 arranged between the reinforcement points 17. The support structure 16 is configured so that it does not touch the mask bead attachment 24. It has a greater wall thickness than the mask bead wall 24 surrounding it in the individual regions (nose bridge region 11, side regions 12, base region 13). Generally, the support structure has wall thickness greater by 1/10 than the mask bead wall 24 surrounding it. The support structure 16 is configured as a thickened arc strand which is formed integrally in the mask bead 10. The support structure 16 can have a round, oval or polygonal shape.

FIG. 4 moreover shows a supporting element 19, which is arranged in the region of a vertex of the connecting structure 20 and, starting from the support structure 16, extends in an hourglass shape in the direction of the mask bead attachment 21. In the present embodiment, the supporting element 19 is integrated in the mask bead wall 24. The supporting element 19 generally has the same wall thickness as the support structure 16. However, the wall thickness of the supporting element 19 may also differ from the wall thickness of the support structure 16.

Figure 5A:
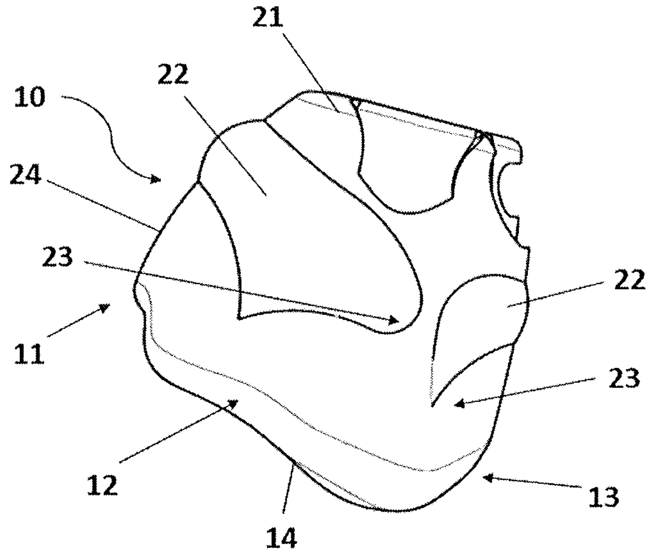
FIG. 5*a* shows a side view of a further embodiment of the mask bead according to the invention with the support structure (not visible), the supporting element (not visible), two adjustment regions and two kink regions.

FIG. 5*a* shows a perspective side view of the mask bead 10 according to the invention, wherein the mask bead wall 24, the nose bridge region 11, the side region 12, the base region 13 and also the bearing region 14 and the mask bead attachment 21 are shown.

Adjustment regions 22 are also shown. The adjustment regions 22 are formed by the support structure (not shown) and by at least one supporting element (not shown). The adjustment regions 22 have kink regions 23 of U-shaped or V-shaped design.

The adjustment regions 22 are integrated in the mask bead wall 24 and have the same wall thickness as the mask bead wall 24. However, in a further embodiment, they can also have different wall thicknesses. When pressure is applied to the mask bead 10, the adjustment regions 22 are designed to form a convexity, as a result of which the distance between the support structure 16 (not shown) and the mask bead attachment 21 is reduced. The convexity can be formed peripherally around the mask bead in the region of the adjustment region 22. In the present embodiment, the adjustment regions 22 have a different extent, such that there is a first, larger adjustment region and a second, smaller adjustment region. The extent of the adjustment regions 22 is dictated by the arrangement of the supporting element 19.

FIG. 5*a* thus shows the mask bead 10 according to the invention in which, in the present embodiment, the adjustment regions 22 are formed by a supporting element 19 (not shown) arranged laterally at the connecting structure 18. Together with the support structure 16, the supporting element 19 defines the shape of the kink region 23.

Figure 5B:
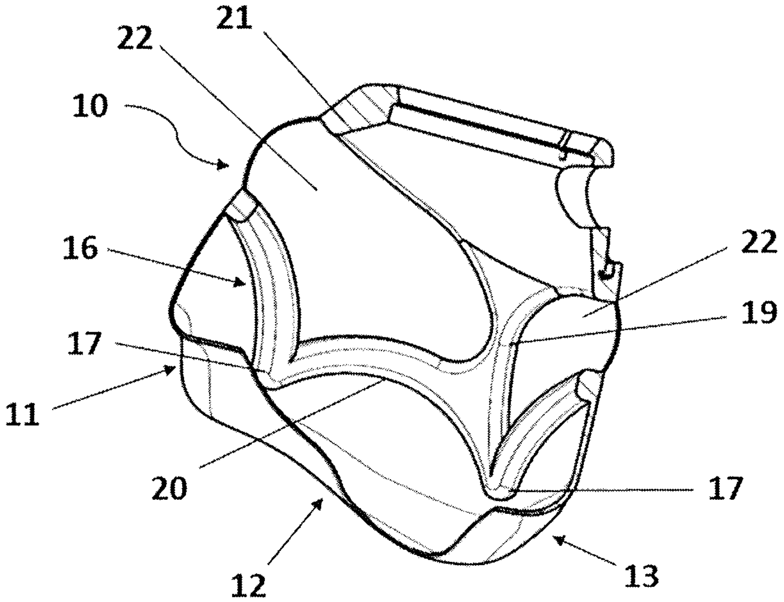
FIG. 5*b* shows a longitudinal section through the embodiment of the mask bead according to the invention shown in FIG. 5*a*, with the support structure, the supporting element, two kink regions and two adjustment regions.

FIG. 5*b* shows a longitudinal section through the embodiment of the mask bead 10 according to the invention shown in FIG. 5*a*. It shows the vault-shaped structure 16, the reinforcement points 17 and the connecting structure 18. The supporting element 19 is also shown, wherein the supporting element 19 does not widen in an hourglass shape starting from a vertex of the connecting structure 18, and instead it is formed by a lateral portion of the arch-shaped connecting structure 18. The adjustment regions 22 are delimited by the support structure 16, the supporting element 19 and the mask bead attachment 21. The adjustment regions 22 can be made of a more elastic, thinner material, or a different material, than the regions of the mask bead 10 surrounding them. The adjustment regions 22 may have internal stiffening structures which, for example, can be formed by different material hardnesses.

Figure 6A:
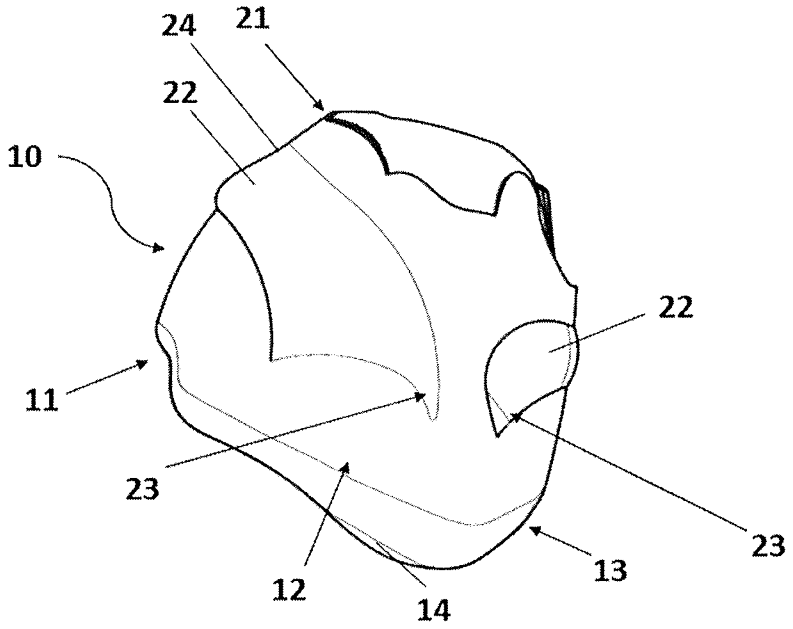
FIG. 6*a* shows a further alternative embodiment of the mask bead according to the invention with the support structure (not shown), the supporting element (not shown), two kink regions and two adjustment regions.

FIG. 6*a* shows a further alternative embodiment of the mask bead 10 according to the invention, with the mask bead attachment 21, the support structure (not shown), the supporting element (not shown), two kink regions 23 and two adjustment regions 22.

It shows an embodiment with two adjustment regions 22 of different size, namely a first and a second adjustment region 22. The first and the second adjustment region 22 are determined by the position of the supporting element (not shown) at the support structure (not shown). The first and the second adjustment region 22 are configured to form a convexity of the mask bead wall 24 under pressure. The adjustment regions each have kink regions 23 which, in the present embodiment, are V-shaped. Optionally, the kink regions 23 can also be U-shaped.

Figure 6B:
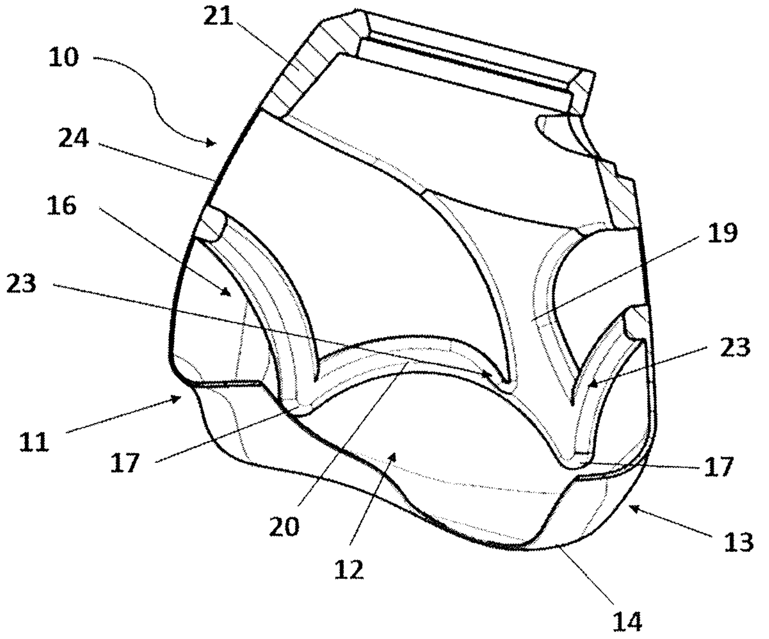
FIG. 6*b* shows a longitudinal section through the embodiment of the mask bead according to the invention shown in FIG. 6*a*, with the support structure, the supporting element, two adjustment regions, and two kink regions in the non-kinked state.

FIG. 6*b* shows an axial longitudinal section through the embodiment of the mask bead 10 according to the invention shown in FIG. 6*a*, with the support structure 16, the supporting element 19, two adjustment regions 22 and two kink regions 23 in the non-kinked state. The mask bead 10 according to the invention has the supporting element 19 which extends in an hourglass shape from the support structure 16 in the direction of the mask bead attachment 21. The support structure 16 has the reinforcement points 17 and also an arch-shaped connecting structure 18. The kink region 23 is formed at the transition of the support structure 16 to the supporting element 19. In the region of the kink region 23, the support structure 16 has a reduction of the wall thickness. The kink region 23 can be enlarged by reducing the wall thickness of the support structure 16, such that the adjustment region 22 formed by the kink region 23 is enlarged.

Figure 6C:
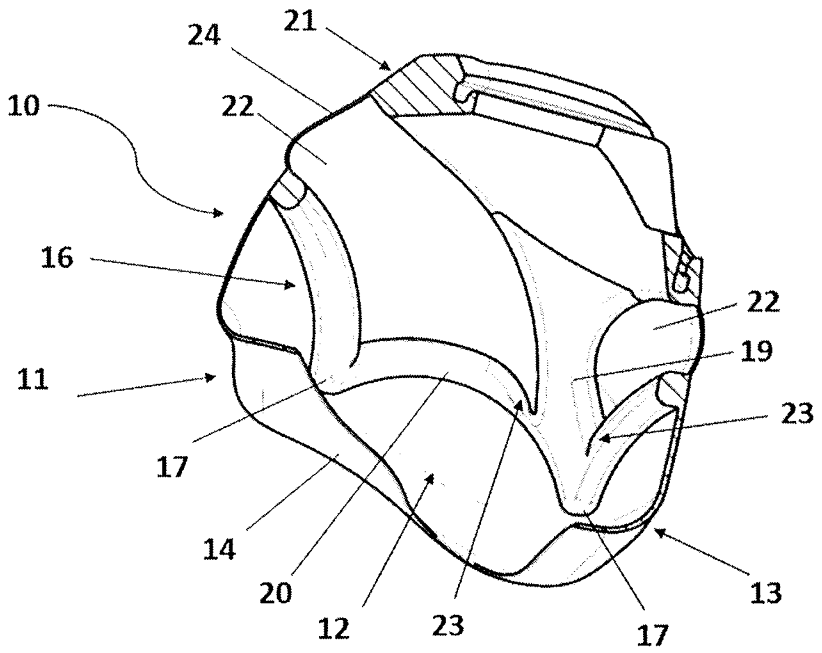
FIG. 6*c* shows a longitudinal section through the embodiment of the mask bead according to the invention shown in FIGS. 6*a* and 6*b*, with the support structure, the supporting element, two adjustment regions, and two kink regions in the kinked state.

FIG. 6*c* shows an axial longitudinal section through the embodiment of the mask bead 10 according to the invention shown in FIGS. 6*a* and 6*b*, with the support structure 16, the supporting element 19, adjustment regions 22 and two kink regions 23 in the non-kinked state. The support structure 16 has the reduced wall thickness described with reference to FIG. 6*b*, and the supporting element 19 is arranged laterally at the connecting structure 18 of the support structure 16, as a result of which a first, large adjustment region and a second, smaller adjustment region 22 are formed. The figure shows the mask bead 10 according to the invention in the kinked state, i.e. with pressure applied to the mask bead 10 in the fitted state. The figure shows that the mask bead wall 24 is convex in this kinked state. Thus, the distance between the support structure 16 and the mask bead attachment 21 has been reduced, such that the surplus mask bead wall 24 bulges outward.

Figure 7:
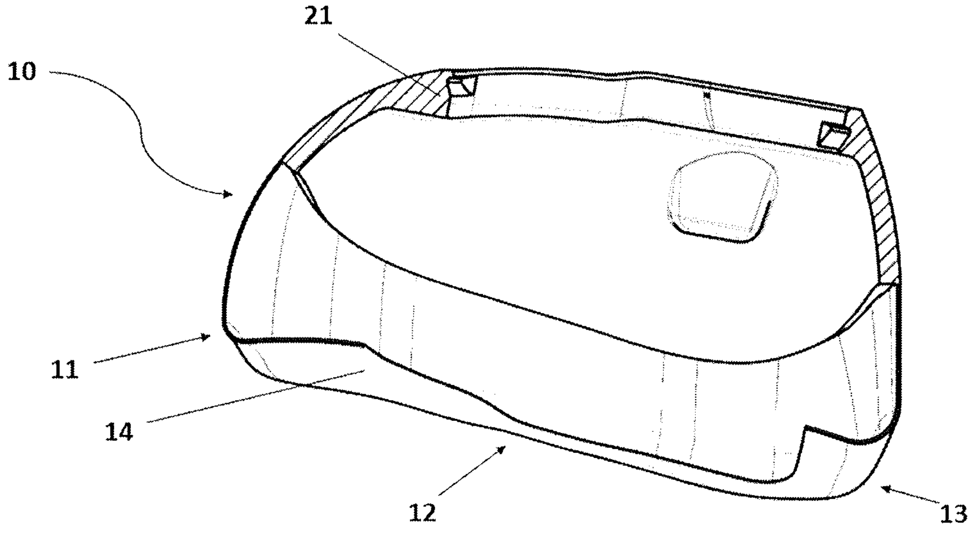
FIG. 7 shows a longitudinal section through an embodiment of a mask bead according to the invention.

FIG. 7 shows a longitudinal section through an embodiment of a mask bead 10 according to the invention. The nose bridge region 11, the side region 12, the base region 13 and also the bearing region 14 are shown here. The figure also shows the support structure 16.

In the present embodiment, the support structure 16 has a wall thickness of between 1.8 mm and 2 mm. The wall thickness of the support structure 16 can vary. Thus, part of the support structure 16 formed adjacent to the nose bridge region 11 can have a smaller wall thickness (for example 1.6 mm) than a part of the support structure 16 (wall thickness 2.0 mm, for example) formed adjacent to the base region 13.

As is shown in FIG. 7, the mask bead 10 has different wall thicknesses. Thus, the nose bridge region 11 has a wall thickness of between 0.2-0.7 mm, in particular 0.35 mm.

The side region 12 has a lesser wall thickness than the support structure 16 surrounding it. In the present embodiment, the side region 12 has a wall thickness of 1.6 mm.

The base region 13 generally has a greater wall thickness than the nose bridge region 11 lying opposite it. The base region generally has a wall thickness of 0.5-1.2 mm. In the present embodiment, the base region 13 has a wall thickness of 0.6 mm.

Figure 8:
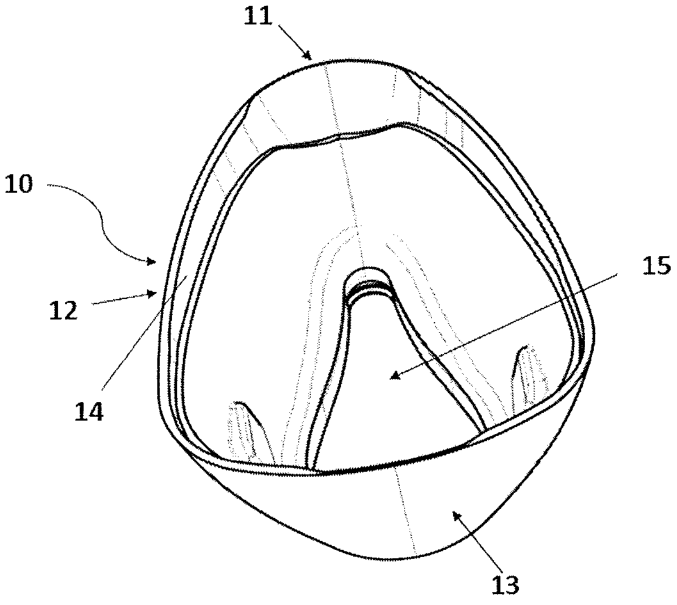
FIG. 8 shows a perspective view of an opening of the mask bead according to the invention.

FIG. 8 shows a perspective view of the opening 15 of the mask bead 10 according to the invention shown in FIG. 7. It shows the nose bridge region 11 and also the side regions 12 and the base region 13 and the bearing region 14. The mask bead 10 has a different wall thickness, wherein the difference between the wall thickness of the support structure 16 and of the mask bead wall 22 surrounding the latter is small, in particular between 0.2 mm and 0.4 mm.

Figure 9:
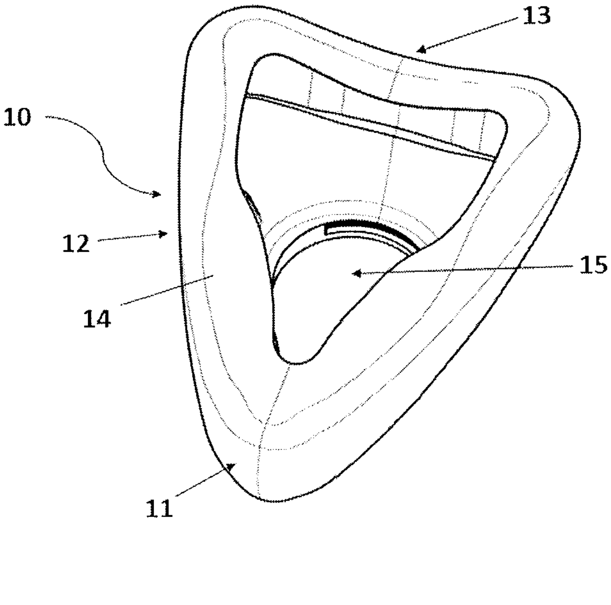
FIG. 9 shows a perspective view of the opening of the mask bead according to the invention with a bearing region.

FIG. 9 shows a perspective view of the opening 15 of the mask bead 10 according to the invention with the bearing region 14. It also shows the nose bridge region 11, the side regions 12 and the base region 13, which are arranged around the opening 15. The bearing region 14 extends peripherally about the opening 15 and is configured as a sealing lip.

LIST OF REFERENCE NUMERALS

10 mask bead
11 nose bridge region
12 side region
13 base region
14 bearing region
15 opening
16 support structure
17 reinforcement points
18 connecting structure
19 supporting element
20 arch
21 mask bead attachment
22 adjustment region
23 kink region
24 mask bead wall
25 transition region

What is claimed is:

1. A mask bead for a patient interface, wherein the bead comprises a nose bridge region, one or more side regions, a base region, a mask bead attachment, and a bearing region configured to be disposed on a patient in use, and wherein the bearing region extends from the side regions and the base region and also the nose bridge region to an opening and is designed as a sealing lip which frames the opening which serves at least for an introduction of a nose of the patient, the mask bead being formed from at least one elastic material and comprising at least one support structure which is designed to in part face the bearing region and to in part face the mask bead attachment and comprises at least two reinforcement points and at least one connecting structure which is designed as an arch between the two reinforcement points.

2. The mask bead of claim 1, wherein the support structure surrounds the opening by at least two thirds.

3. The mask bead of claim 1, wherein the reinforcement points in the mask bead are arranged in a region of the bearing region or are arranged lying on the bearing region.

4. The mask bead of claim 1, wherein, starting from the at least one connecting structure of the support structure, a supporting element is formed which widens in a direction of a mask bead attachment.

5. The mask bead of claim 4, wherein the supporting element is formed running centrally or laterally from the connecting structure.

6. The mask bead of claim 4, wherein at least one kink region is formed at the at least one transition of the support structure to the supporting element.

7. The mask bead of claim 6, wherein at least one of the kink regions is formed by a reduction of a thickness of the support structure.

8. The mask bead of claim 6, wherein the support structure and the at least one kink region form at least one adjustment region.

9. The mask bead of claim 1, wherein the reinforcement points are formed at a transition of the nose bridge region to a side region.

10. The mask bead of claim 1, wherein the reinforcement points of the support structure are arranged in at least one side region.

11. The mask bead of claim 1, wherein the at least one connecting structure is formed over the nose bridge region of the mask bead, and wherein the reinforcement points delimiting the connecting structure are arranged at respective side regions of the mask bead separated by the opening.

12. The mask bead of claim 1, wherein at least one connecting structure is formed over a side region of the mask bead, and wherein reinforcement points delimiting the connecting structure are arranged on a common side region of the mask bead.

13. The mask bead of claim 1, wherein the support structure has a wall thickness that is 1/12 to 1/8 thicker than a respective region in which it is formed.

14. The mask bead of claim 1, wherein the support structure has a wall thickness of from 2 mm to 1.8 mm, and a surrounding mask bead wall has a wall thickness of about 1.6 mm.

15. The mask bead of claim 1, wherein the arch faces away from the bearing region.

16. The mask bead of claim 1, wherein at least one kink region is formed at at least one transition of the support structure to a supporting element, the support structure and the at least one kink region forming at least one adjustment region having a wall thickness of from 0.2 mm and 0.7 mm.

17. The mask bead of claim 1, wherein the at least one support structure has a wall thickness of from 2 mm to 1.8 mm, the nose bridge region has a wall thickness of from 0.2 mm to 0.7 mm, the base region has a wall thickness of from 0.5 mm to 1.2 mm and the one or more side regions have a wall thickness of from 1.2 mm to 2.5 mm.

18. The mask bead of claim 1, wherein the reinforcement points are at a transition of the base region to a side region.

19. A mask bead for a patient interface, wherein the bead comprises a nose bridge region, one or more side regions, a base region, a mask bead attachment, and a bearing region configured to be disposed on a patient in use, wherein the bearing region extends from the side regions and the base region and also the nose bridge region to an opening and is designed as a sealing lip which frames the opening which serves at least for an introduction of a nose of the patient, the mask bead being formed from at least one elastic material and comprising at least one support structure which is designed to in part face the bearing region and to in part face the mask bead attachment and comprises a connecting structure between two reinforcement points formed at a transition of the nose bridge region to a side region.

20. The mask bead of claim 19, wherein the support structure surrounds the opening at least by two thirds.

* * * * *